United States Patent [19]

Sick et al.

[11] 4,310,250

[45] Jan. 12, 1982

[54] APPARATUS FOR MONITORING FOR FAULTS IN TRANSLUCENT STRIP MATERIAL

[75] Inventors: Erwin Sick, Icking; Klaus Ostertag, Munich, both of Fed. Rep. of Germany

[73] Assignee: Erwin Sick GmbH, Waldkirch, Fed. Rep. of Germany

[21] Appl. No.: 117,720

[22] Filed: Feb. 1, 1980

[51] Int. Cl.³ .......................................... G01N 21/89
[52] U.S. Cl. .................................. 356/431; 250/572; 356/444
[58] Field of Search ............... 356/444, 443, 430, 431, 356/239; 250/572

[56] References Cited

U.S. PATENT DOCUMENTS

| | | | |
|---|---|---|---|
| 3,331,963 | 7/1967 | Lippke | 250/219 |
| 3,786,265 | 1/1974 | Abilock et al. | 250/209 X |
| 3,841,761 | 10/1974 | Selgin | 356/430 |
| 3,843,890 | 10/1974 | Anthony, Jr. et al. | 250/563 |
| 4,005,926 | 2/1977 | Neale et al. | 356/444 |
| 4,110,047 | 8/1978 | Takahashi | 356/430 |

FOREIGN PATENT DOCUMENTS

| | | |
|---|---|---|
| 1183718 | 12/1964 | Fed. Rep. of Germany . |
| 1297892 | 6/1969 | Fed. Rep. of Germany |
| 1798349 | 11/1971 | Fed. Rep. of Germany . |
| 2127999 | 12/1971 | Fed. Rep. of Germany . |
| 1526375 | 9/1978 | United Kingdom ............... 356/444 |

*Primary Examiner*—John K. Corbin
*Assistant Examiner*—Bruce Y. Arnold
*Attorney, Agent, or Firm*—Townsend and Townsend

[57] ABSTRACT

Apparatus for monitoring for faults in translucent strip material, such as photographic film, comprises a transport device 16, 12, 13, 22 for continuously moving the film 11 in its longitudinal direction and an optical scanning device 23 including a beam divider 21 which divides a single series of scanned light beams 14 into first and second sets of scanned light beams 14a 14b. The first set of light beams 14a is used to carry out transmission measurements on the film as it passes in tensioned condition between two spaced apart rollers 12, 13 and the second set 14b is used to carry out measurements in reflection as the film passes around the surface of a roller 16. The roller 16 has an air permeable surface and air is blown through this surface from the inside of the roller to form an air cushion between the film and the roller.

Faults are detected by the electronic processing circuitry 18 in response to variations in the transmission and reflection measurements carried out by the light detectors 15 and 17.

5 Claims, 1 Drawing Figure

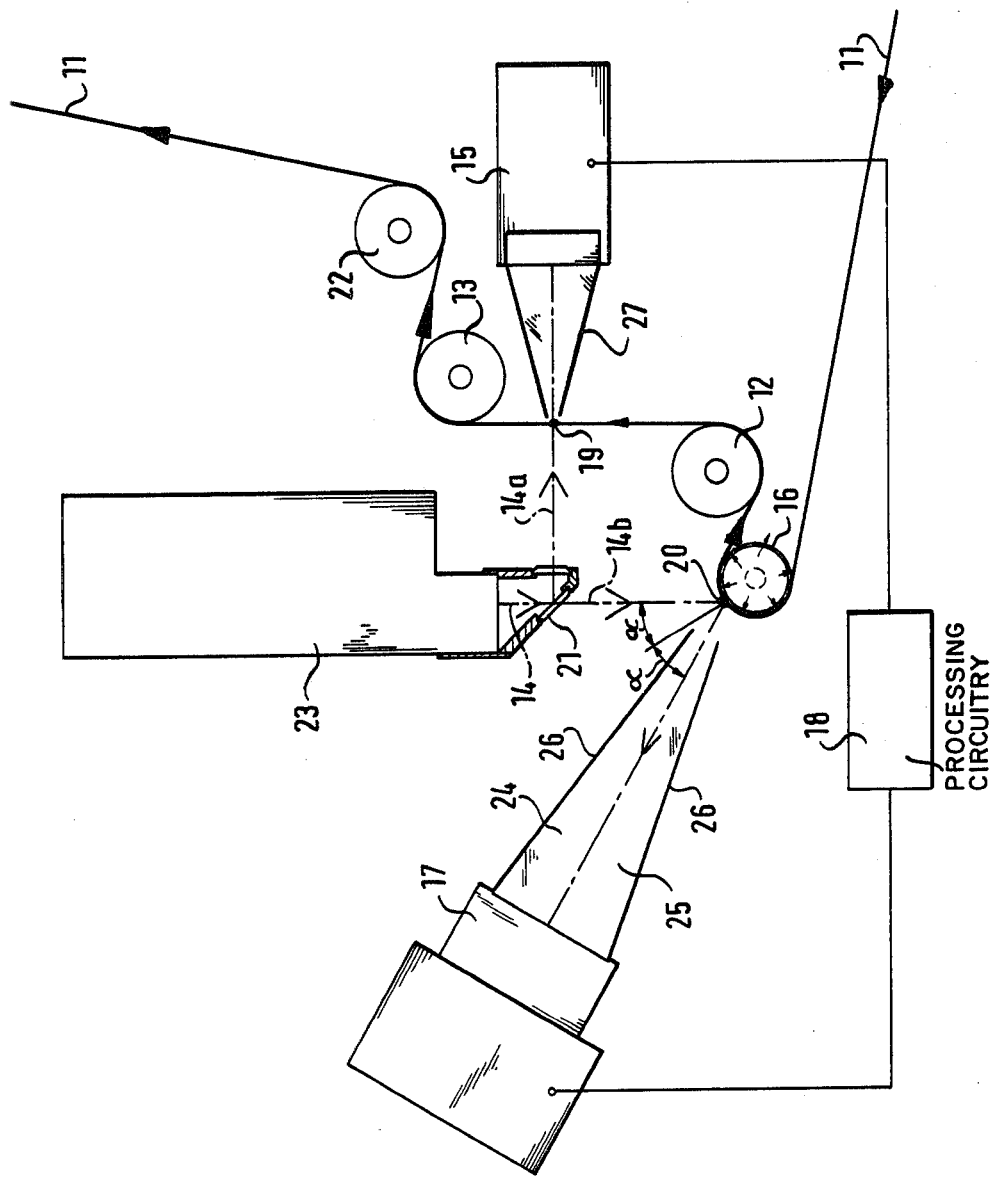

APPARATUS FOR MONITORING FOR FAULTS IN TRANSLUCENT STRIP MATERIAL

The invention relates to an apparatus for monitoring for faults in transparent strip-like material and has particular reference to the detection of faults in photographic film.

A monitoring apparatus is already known for this purpose and generally comprises a transport device for continuously moving a film in its longitudinal direction, an optical scanning device which generates a scanning light bead for scanning the film line-by-line, point-by-point, transversely of its direction of movement and a photoelectric light detecting arrangement including at least one light conducting rod for receiving light from the scanning light bead as modified by the film.

In apparatus of this kind it is necessary to monitor the film for faults both in transmission and also in reflection. This can for example be achieved by guiding the film over a glass roller or a section of a glass cylinder and by projecting a scanning light beam which moves periodically to and fro onto the film in this region. A first light receiver arranged behind the scanning region can receive the transmitted light and a second light receiver arranged in front of the film can receive the reflected light and can detect faults which influence or affect the transmitted, or reflected light.

An arrangement of this kind is, however, disadvantageous because faults, which are not truly present, can be simulated if the glass roller or the section of a glass cylinder are dirty, by the formation of air bubbles between the fiilm and the glass surface and if scratches are present on the glass surface.

The principal object underlying the present invention is thus to provide a monitoring apparatus for monitoring for faults in film material which enables measurements to be taken both in transmission and also in reflection without the two measurements mutually and unfavourably influencing one another. A further object of the present invention is to keep the trouble and expense required to generate the scanning light bead at a very low level.

Further objects and aims of the present invention will become clear from the subsequent description and include the provision of a simple and compact apparatus.

For accomplishing the above objects the invention envisages apparatus for monitoring for faults in translucent strip material such as photographic film, the apparatus comprising a transport device for continuously moving the strip material in its longitudinal direction, an optical scanning device for projecting a series of light beams at the strip for line by line point by point scanning thereof in a direction transverse to its direction of movement and photoelectric detector means with at least one light conducting rod for receiving light from said light beams after impingement of the light from said light beams on the film and characterized in that the strip is forwarded in tensioned condition between two spaced apart rollers, that a first set of the light beams impinge on the strip substantially at right angles thereto in the region between said two rollers, that a first photoelectric detector arrangement is arranged behind the strip to receive light from said first set of light beams, that the strip either before or after both of the said rollers is fed around a further roller and that a second set of light beams is directed onto the strip in this region and that a second photoelectric detector arrangement is provided for light reflected from the strip at said further roller.

Thus, in accordance with the invention, the transmission measurement and the reflection measurement take place at two respective points spaced apart in the longitudinal direction of the strip or film material. For this reason the two light detectors are usefully connected to an electronic processing circuit which contains a store or memory and which coordinates the two spacially separated detection points. The spacial separation of the two detection points which is actually present can thus be cancelled by electronic means. In practice a fault in the film material will generally affect both the transmission and the reflection measurements and the electronic processing circuit can simply consist of a device for delaying the signal from the first measurement for a period of time corresponding to the movement of the film from the point of the first measurement to the point of the second measurement and an and gate which passes an error signal when the measurement at the second measurement point also indicates that a fault is present.

Because the transmission measurement is carried out from that part of the strip of material which is supported in tensioned condition between the two spaced apart rollers optimum conditions are present for effecting this kind of measurement. A certain degree of fluttering of the strip material does not disadvantageously affect the transmission measurement. The reflection measurement would however be considerably disadvantageously influenced by fluttering of the strip material. For this reason the reflection measurement is carried out on the film which is fed around the third or further roller. A particularly favourable and undisturbed movement of the film around this roller is brought about by providing the roller with an air permeable peripheral wall through which air is blown from the inside of the roller towards the outside in order to maintain an air cushion between the strip and the roller. In this way optimum conditions are provided for carrying out the reflection measurement. A transmission measurement would, however, not be possible at this position because of the special construction of the third roller.

The generation of the series of light beams for projection onto the strip material is ensured in particularly simple fashion by arranging for the light beams, which are preferably produced by a single scanning device which for example incorporates a laser and a mirror wheel, to be divided into first and second sets of light beams by a beam divider and for the distances traversed by the first and second sets of light beams from the beam divider to the strip material to be equal. In this way the scanning light beads, which are projected onto the strip material at two points which are spaced apart in the longitudinal direction of the strip material, have the same form and intensity.

A particularly straightforward spacial construction is achieved if the planes of the film at the two scanning points are inclined at an angle one to the other such that one of the sets of light beams lies in the extension of the undivided series of light beams and the other set of light beams is reflected out of the series of light beams by the beam divider. Thus, for generating two scanning light beads only a simple beam divider is required in addition to a single device for generating a scanning light bead.

The invention will now be described in further detail and by way of example only with reference to the accompanying drawing, the single FIGURE of which shows a schematic side view of an apparatus for monitoring for faults in translucent strip material.

As seen in the drawing continuously moving film material 11 is drawn in the direction illustrated by the arrows by means of a film transport device which is not illustrated in detail but which includes in customary fashion and in addition to the rollers 16, 12, 13 and 22 a film winding device which draws film via a film tensioner from a spool of film material. The film 11 is led from a generally horizontal direction around an apertured roller 16 and pressurized air is supplied to the interior of the apertured roller 16 in order to form a defined air cushion between the surface of the roller and the film. This is useful, apart from other reasons, in order to avoid drawing in air bubbles and disturbing the optical measurement procedure. In addition travelling waves in the longitudinal direction of the film are avoided by the presence of the air cushion.

After the film 11 has passed around the roller 16 by somewhat more than 180° so that it is now moving in approximately the opposite direction it reaches a guide roller 12 and is guided around this roller into the vertical direction. After traversing a predetermined path the film is once more turned around a further guide roller 13 through an angle of approximately 90° from whence it is guided in the opposite direction to the incoming film around another guide roller 22. The film then leaves this further roller 22 in an approximately vertical direction and is passed on for a subsequent treatment or use and eventual winding by the winding roller (not shown) of the transport device.

An optical scanning device 23 is located generally above the apertured roller 16 and generates a series of scanning light beams 14 in a manner known per se by means of a laser and a mirror wheel and also lenses and a strip-like concave mirror (not shown). The series of light beams 14 carry out a continuous and periodic scanning movement at right angles to the plane of the drawing, i.e. the beams 14 can be regarded as moving vertically downwardly through a vertically directed plane arranged at right angles to the plane of the drawing. A beam divider 21 is provided at the lower end of the scanning device 23 and is inclined at an angle of 45° to the vertical direction. The beam divider, which can be a half-silvered mirror thus divides the series of light beams 14 into first and second sets of light beams 14a, 14b. The first set of light beams 14a are reflected at right angles to the right out of the series of light beams 14 and the second set of light beams 14b are directed vertically downwardly as an extension of the series of light beams 14 and impinge on the film at the point 20 at an angle α to the surface of the roller 16. Light specularly reflected from the point 20 at the angle of reflection α reaches the centre of a light detection device 17 which can contain one or more light conducting rods and cylindrical lenses which extend parallel to the scanning direction, i.e. at right angles to the plane of the drawing.

Light reflected in the regions 24, 25 can, if required, be detected separately from the specularly reflected light and can be processed in the electronic processing circuit 18.

An aperture stop 26 arranged on both sides of the regions 24, 25 prevents stray light from reaching the light detector 17.

The first set of beams 14a which is reflected sideways out of the series of light beams 14 impinges at right angles of the film 11 at the point 19. It is important that the distances of the impingement points 19, 20 from the beam divider 21 are the same.

Directly behind the impingement point 19 there is located a further light detector 15 which preferably operates only with a single light conducting rod and, if required, a cylindrical lens arranged in front of the light conducting rod. A photodetector is provided at at least one end face of each of the light conducting rods for converting the light which enters the light conducting rod into an electrical signal.

An aperture stop 27 is arranged between the film 11 and the light receiver 15 and once more reduces the amount of stray light which can reach the light detector.

Whereas the light detector 17 responds to specularly reflected light the light detector 15 detects apertures in the film, or variations in the transparency or translucency thereof.

The particularly advantageous illumination of the two detection points 19 and 20 by one and the same scanning device is achieved by virtue of the fact that the film is guided through an angle of approximately 90° between the scanning point 20, the roller 12 and the scanning point 19. The film 11 which extends between the scanning points 19 and 20 and also the first and second sets of beams 14a, 14b thus together form an approximately quadrangular figure.

If desired, transmission on the one hand and also reflection on the other hand can be separately detected rather than by combining the two error signals in the electronic processing circuit 18. The precise layout of the electronic processing circuit 18 will depend on the nature of the faults which it is desired to detect. As a general rule faults in the film material will influence both the transmitted and the remitted or reflected light and the electronic processing circuit can conveniently include delay circuitry such as a store for storing the signal from the first light detector 17 for a period equal to the movement of the film from the scanning point 20 to the scanning point 19 and this signal together with the signal from the light detector 15 can then be subsequently be applied to the two inputs of an And-gate or other desired logic element. It will be appreciated that the present invention is primarily concerned with the overall layout of the fault monitoring apparatus and not with the processing of the individual fault signals which will be readily understood by those skilled in the art.

We claim:

1. Apparatus for monitoring for faults in translucent strip material comprising:
   first and second spaced apart rollers for supporting the strip material;
   transport means for continuously moving the strip material in tensioned condition between the first and second spaced apart rollers;
   optical scanning means for projecting first and second light beams at said strip material to effect line scanning thereof in a direction transverse to its direction of transport with said first light beam impinging on said strip material substantially at right angles thereto between said first and second rollers;
   a first photoelectric detector means disposed behind said strip material to receive light transmitted therethrough;
   a third roller having an air permeable peripheral wall through which air is blown from the inside to the outside to maintain an air cushion between said strip material and said third roller, said second light beam being directed onto said strip material for reflection from the surface thereof as said strip material passes around said third roller; and a second photoelectric detection means for detecting light reflected from the surface of said strip material.

2. Apparatus according to claim 1, wherein both said first and second photoelectric detection means are connected to an electronic processing circuit which contains a store which coordinates signals received from said first and second photoelectric detection means.

3. Apparatus according to claim 1, wherein said optical scanning means includes a beam divider for splitting an incident beam of light into said first and second light beams and wherein the distances traversed by said first and second light beams from the beam divider to said strip material are equal.

4. Apparatus according to claim 3, wherein the tangent planes to said strip material at the points of incidence of said first and second light beams lie at an angle one with the other such that one of said first and second light beam falls normally on said strip material and the other of said beams falls at an oblique angle on the strip material as it passes around the third roller.

5. Apparatus for monitoring for faults in translucent strip material, said apparatus comprising:

a roller;

transport means for continuously moving the strip material around said roller, said roller having an air permeable wall through which air is blown from the inside to the outside to maintain an air cushion between said strip material and said roller;

optical scanning means for directing a light beam onto the surface of said strip material as it passes around said roller to effect line scanning thereof; and photoelectric detection means for receiving light remitted from the surface of said strip material.

* * * * *